(12) United States Patent
Limmert et al.

(10) Patent No.: US 8,134,146 B2
(45) Date of Patent: Mar. 13, 2012

(54) HETEROCYCLIC RADICAL OR DIRADICAL, THE DIMERS, OLIGOMERS, POLYMERS, DISPIRO COMPOUNDS AND POLYCYCLES THEREOF, THE USE THEREOF, ORGANIC SEMICONDUCTIVE MATERIAL AND ELECTRONIC OR OPTOELECTRONIC COMPONENT

(75) Inventors: Michael Limmert, Dresden (DE); Olaf Zeika, Dresden (DE); Martin Ammann, Dresden (DE); Horst Hartmann, Dresden (DE); Ansgar Werner, Dresden (DE)

(73) Assignee: Novaled AG, Dresden (DE)

( * ) Notice: Subject to any disclaimer, the term of this patent is extended or adjusted under 35 U.S.C. 154(b) by 482 days.

(21) Appl. No.: 11/688,777

(22) Filed: Mar. 20, 2007

(65) Prior Publication Data
US 2007/0252140 A1    Nov. 1, 2007

(30) Foreign Application Priority Data
Mar. 21, 2006    (EP) .................................... 06005687

(51) Int. Cl.
*H01L 51/00* (2006.01)
*C07D 207/00* (2006.01)
*C07D 209/56* (2006.01)
*C07D 221/00* (2006.01)
*C07D 239/00* (2006.01)
*C07D 241/00* (2006.01)
*C07D 245/00* (2006.01)
*C07D 307/00* (2006.01)
*C07D 333/00* (2006.01)

(52) U.S. Cl. ................ 257/40; 438/99; 544/1; 544/247; 544/250; 544/344; 546/62; 546/94; 548/100; 548/113; 549/16; 549/43; 549/50; 549/385; 549/469

(58) Field of Classification Search .......................... None
See application file for complete search history.

(56) References Cited

U.S. PATENT DOCUMENTS

| | | | |
|---|---|---|---|
| 2,566,208 A | 8/1951 | Jenkins | |
| 3,083,242 A | 3/1963 | Ramsden | |
| 3,226,450 A | 12/1965 | Blazejak et al. | |
| 3,558,671 A | 1/1971 | Martin | |
| 3,563,751 A | 2/1971 | Cohen | |
| 4,003,943 A | 1/1977 | Fukunaga | |
| 4,066,569 A | 1/1978 | Lim | |
| 4,133,821 A | 1/1979 | West et al. | |
| 4,618,453 A | 10/1986 | Kim | |
| 4,960,916 A | 10/1990 | Pazik et al. | |
| 5,093,698 A | 3/1992 | Egusa | |
| 5,110,835 A | 5/1992 | Walter et al. | |
| 5,247,226 A | 9/1993 | Sato et al. | |
| 5,281,730 A | 1/1994 | Zambounis et al. | |
| 5,292,881 A | 3/1994 | Berneth et al. | |
| 5,393,614 A | 2/1995 | Nakada | |
| 5,556,524 A | 9/1996 | Albers | |
| 5,811,833 A | 9/1998 | Thompson | |
| 5,840,217 A | 11/1998 | Lupo et al. | |
| 5,922,396 A | 7/1999 | Thompson et al. | |
| 6,013,384 A | 1/2000 | Kido et al. | |
| 6,013,982 A | 1/2000 | Thompson et al. | |
| 6,103,459 A | 8/2000 | Diel et al. | |
| 6,207,835 B1 | 3/2001 | Reiffenrath et al. | |
| 6,824,890 B2 | 5/2001 | Bazan et al. | |
| 6,350,534 B1 | 2/2002 | Boerner et al. | |
| 6,423,429 B2 | 7/2002 | Kido et al. | |
| 6,524,728 B1 | 2/2003 | Kijima et al. | |
| 6,700,058 B2 | 3/2004 | Nelles et al. | |
| 6,747,287 B1 | 6/2004 | Toguchi et al. | |
| 6,908,783 B1 | 7/2005 | Kuehl et al. | |
| 6,972,334 B1 | 12/2005 | Shibanuma et al. | |
| 7,081,550 B2 | 7/2006 | Hosokawa et al. | |
| 7,345,300 B2 | 3/2008 | Qin | |
| 2003/0064248 A1 | 4/2003 | Wolk | |
| 2003/0165715 A1 | 9/2003 | Yoon et al. | |
| 2003/0234397 A1 | 12/2003 | Schmid et al. | |
| 2004/0068115 A1 | 4/2004 | Lecloux et al. | |
| 2004/0076853 A1 | 4/2004 | Jarikov et al. | |
| 2005/0023974 A1 | 2/2005 | Chwang et al. | |
| 2005/0040390 A1 | 2/2005 | Pfeiffer et al. | |
| 2005/0042390 A1 | 2/2005 | Pfeiffer, et al. | |
| 2005/0061232 A1 | 3/2005 | Werner et al. | |
| 2005/0072971 A1 | 4/2005 | Marrocco et al. | |
| 2005/0086251 A1 | 4/2005 | Hatscher et al. | |
| 2005/0110009 A1 | 5/2005 | Blochwitz-Nimoth et al. | |
| 2005/0121667 A1 | 6/2005 | Kuehl et al. | |
| 2006/0049397 A1 | 3/2006 | Pfeiffer et al. | |
| 2007/0026257 A1 | 2/2007 | Begley et al. | |
| 2007/0058426 A1 | 3/2007 | Sokolik et al. | |
| 2007/0090371 A1 | 4/2007 | Drechsel et al. | |

(Continued)

FOREIGN PATENT DOCUMENTS

CA        2549309          9/2005

(Continued)

OTHER PUBLICATIONS

Ludvik et al., caplus an 1988:578804.*
Shkrob, caplus an 2009:1306254.*
Mark R. DeLuca, et al., The para-Toluenesulfonic Acid-Promoted Synthesis of 2-Substituted Benzoxazoles and Benzimidazoles from Diacylated Precursors, Tetrahedron, vol. 53, No. 2, pp. 457-464, 1997.
Massimo Curini, et al., Ytterbium Triflate Promoted Synthesis of Benzimidazole Derivatives, Synlett, No. 10, pp. 1832-1834, 2004.
M. Ross Grimmett, Imidazole and Benzimidazole Synthesis, Table of Contents, pp. 1-10, Academic Press, Harcourt Brace & Company, Publishers, London, San Diego, New York, Boston, et al., 1997.

(Continued)

*Primary Examiner* — Sun Jae Loewe
(74) *Attorney, Agent, or Firm* — Sutherland Asbill & Brennan LLP

(57) ABSTRACT

The present invention relates to heterocyclic radicals or diradicals, the dimers, oligomers, polymers, dispiro compounds and polycycles thereof, to the use thereof to organic semiconductive materials and to electronic and optoelectronic components.

13 Claims, No Drawings

U.S. PATENT DOCUMENTS

| | | | |
|---|---|---|---|
| 2007/0116984 A1 | 5/2007 | Park et al. |
| 2007/0145355 A1 | 6/2007 | Werner et al. |
| 2007/0249148 A1 | 10/2007 | Werner et al. |
| 2008/0103315 A1 | 5/2008 | Egawa et al. |
| 2008/0122345 A1 | 5/2008 | Sakata et al. |
| 2008/0145708 A1 | 6/2008 | Heil et al. |
| 2008/0265216 A1 | 10/2008 | Hartmann et al. |
| 2009/0001327 A1 | 1/2009 | Werner et al. |

FOREIGN PATENT DOCUMENTS

| | | |
|---|---|---|
| CH | 354065 | 5/1961 |
| CH | 354066 | 5/1961 |
| DE | 19836408 | 2/2000 |
| DE | 10261662 | 7/2004 |
| EP | 1000998 | 5/2000 |
| JP | 61254582 | 11/1986 |
| JP | 63172274 | 7/1988 |
| JP | 63172275 | 7/1988 |
| JP | 04338760 | 11/1992 |
| JP | 7168377 | 7/1995 |
| JP | 2004010703 | 1/2004 |
| JP | 2004335557 | 11/2004 |
| JP | 2005167175 | 6/2005 |
| JP | 2005/525696 | 8/2005 |
| WO | WO 03/088271 | 10/2003 |
| WO | WO 03/104237 | 12/2003 |
| WO | WO 2006/067800 | 6/2006 |
| WO | WO 2008/022633 | 2/2008 |

OTHER PUBLICATIONS

Alan M. Jefferson and Hans Suschitzky, New Route to Necleophilically Substituted o-Phenylenediamines, J.C.S. Chem. Comm, pp. 189-190, 1997.

Helmut Quast and Edeltraud Schmitt, Note Regarding the Quaternization of Heterocycles, Institute of Organic Chemistry at the University of Wurzburg, 101, pp. 4012-4014, 1968.

Takashi Muramatsu, et al, Preparation and Properties of a Novel Heterocyclic Dispiro Compound, 3,10-Diaza-N,N-dimethyldispiro[5.0.5.3]pentadeca-1,4,8,11-tetraene, Chemistry Letters, pp. 151-152, 1996.

J. Ludvik, F. Pragst, et al., Electrochemical Generation of Triplet States, Journal of Electroanalytical Chemistry, No. 180, pp. 141-156, 1984.

Jurgen Heinze, et al., Polarographic Studies of the Conformation of 1,2,3,4,5-pentaarylimidazolium Cations, The Institute for Physical Chemistry at the University of Freiburg, pp. 1-22, 1972.

Kin-ya Akiba, et al., Direct Synthesis of 2,2-Diarly-3-methyl-2,3-dihydrobenzothiazoles from 3-Methyl-2,3-dihydrobenzothiazole-2-thione and Some Mechanistic Aspects, Bulletin of the Chemical Society of Japan, vol. 52 (1), pp. 156-159, 1979.

Abhishek P. Kulkarni, Electron Transport Materials for Organic Light-Emitting Diodes, Chemistry of Materials, 16, pp. 4556-4573, 2004.

Japanese Office Action which issued in Japanese counter part Application No. 2007-075684 (English Translation) (Jul. 27, 2010).

European Office Action for EP Application No. 07723467.2 mailed Oct. 4, 2011.

Gritzner et al., 1984, "Recommendations on Reporting electrode Potentials in Nonaqueous Solvents," Pure & Appl. Chem., 56(4):461-466.

Noviandri et al., 1999, "The Decamethylferrocenium/Decamethylferrocene Redox Couple: A Superior Redox Standard to the Ferrocenium/Ferrocene Redox Couple for Studying Solvent Effects on the Thermodynamics of Electron Transfer," J. Phys. Chem. B, 1999, 103:6713-6722.

Parsons, 1973, "Manual of Symbols and Terminology for Physicochemical Quantities and Units, Appendix III, Electrochemical Nomenclature," International Union of Pure and Applied Chemistry—Division of Physical Chemistry, Butterworths—London, pp. 503-516.

Ludvik, J. and Pragst, F. et al., "Electrochemical generation of triplet states," Journal of Electroanalytical Chemistry, No. 180, pp. 141-156, (1984).

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).

A. R. Siedle and R. B. Johannesen, "Reduction of the 1,3-dithiolium cation with hexacarbonylvanadate" Journal of Organic Chemistry Bd. 4-, NR. 13 1975, Seite 2202, XP002396000, Verbindungen 1 und 2, Seite 2202.

H. Jadamus, Q. Fernando and H. Freiser, "metal-ion induced rearrangements of bisbenzthiazolines to Schiff-base chelates", Journal of the American Chemical Society, Bd. 86, 1964, Seiten 3056-3059, XP002396001, Verbindung II, Seite 3056. Verbindungen Va-c, Seite 3058.

E. J. Corey, F. A. Carey and R. .A Winter: 1,2,4 "Stereospecific syntheses of olefins from 1, 2-thionocarbonates and 1,2-thrithiocarbonates, Trans-cycloheptene" Journal of the American Chemical Society, Bd. 87, Nr. 4, 1965, Seiten 934-935, XP002396002, Verbindung V, Seite 935.

E. Bayer and E. Breitmaier, "Die reaktion 1, 2, 4 von Benzil mit 2-Aminothiopheno I" Tetrahedron Letters, Bd. 15 1966, Seiten 1689-1693, XP002396003, Verbindung II, Seite 1689.

H. G. Mautner, "Potential deoxyribonucleic acid cross-linking agents. 8,8'-bispurines", Journal of Organic Chemistry Bd. 26, 1961, Seiten 1914-1917, XP002396004 Verbindung I, Seite 1915.

R. C. Elderfield and E. C. McClenachan, "Pyrolisis of the products of the reaction of o-aminobenzenethiols with ketones", Journal of the American Chemical Society, Bd. 82, 1960, Seiten 1982-1988, XP002396005, Verbindung VII, Seite 1983.

M. G. Miles, J. S. Wager and J. D. Wilson: 1, 2, 7, "Reactions of 4,5-dicyano-1,3-dithiole-2-thione and 1,3-dithiol-2-one with tervalent phosphorous compounds", Journal of Organic Chemistry, Bd. 40, Nr, 18, 1975, Seiten 2577-2582, XP002396006, Verbindung 5, Scheme II, Seite 2579.

Disclosure Under 37 C.F.R. Section 1.56 for U.S. Appl. No. 11/688,777 submitted herewith, 2010.

Long, M., "41.4: New Capabilities in Vacuum Thermal Evaporation Sources for Small Molecule OLED Manufacturing", SID 06 Digest, pp. 1474-1476, 2006.

Akutagawa, T. et al. "Multi Electron and Proton-Transfer System Based on 2,2'-biimidazole derivatives," Science and Technology of Syn. Metals, 1994, 346.

Alonso, R. A. et al. "Photostimulated Reaction of Diphenylarsenide and Diphenylstibide Ions with Haloaromatic Compounds by the Srnl Mechanism. Electron Transfer vs. Bond Breaking of the Radical Anion Intermediate," J. Org. Chem. (1982) 47(1) pp. 77-80.

Auch et al. "Eine neue Synthese und die Kristallstrukturanalyse von., Krokonat-Blau . . . ," Chem. Ber. 120, 1691-1696 (1987), extract, pp. 1691-1693, 6 total pages.

Bach, U. et al. "Solid-state dye-sensitized mesoporous $TiO_2$ solar cells with high photon-to-electron conversion efficiencies," Nature, vol. 395, Oct. 8, 1998, pp. 583-585.

Bamgboye, T.T. et al. "Lewis acidity of Ph2SbX3, wherein X=Cl or Br. Crystal structures of Ph2SbC13*H20 and Ph2SbBr3*MeCN," J. of Organometallic Chem. vol. 362, Feb. 28, 1989, pp. 77-85.

Bard, A. J., Faulkner R.J., Electrochemical Methods: Fundamentals and Applications, Wiley, 2nd Ed., 2000 (Chapter 6).

Barton, D.H.R. et al. "Comparative Arylation Reactions with Pentaphenylbismuth and with Triphenylbismuth Carbonate," J. Chem. Soc. Chem. Commun. (1980) 17, pp. 827-829.

Baumgartel, H. et al., "Polarographische Untersuchungen zur Konformation von 1.2.3.4.5-pentaarylimidazoliumkationen," Ber. Bunsenges (1972) 76/2, 94-100.

Baumgartel, H. et al., "Uber eine neue Synthese von tetraaryl-imidazolen und pentaaryl-imidazolium-salzen," Chem. Ber. (1968), 101, 3504.

Bhattacharya, S.N. et al. "Preparation & Characterization of Some Triarylarsenic & Triarylantimony Mixed Halides & Related Compounds," Indian J. Chem. 16A (1978) pp. 778-781.

Blinka et al. "Octacyanotetramethylenecyclobutane Dianioin and its Anion-Radical," Tetrahedron Lett. (1983). vol. 24, No. 1567-1568.

Blochwitz, J., et al., "Low voltage organic light emitting diodes featuring doped phthalocyanine as hole transport material," Applied Physics Letters, vol. 73, No. 6, Aug. 10, 1998, pp. 729-731.

Bonati, F. et al. "Reactions of C-imidazolyllithium derivatives with Broup Ib compounds: tris[micro-(1-alkylimidazolato-N3, C2)]trigold (I) and -silver (I)," J. Organomet. Chem. 1989, 375, pp. 147-160.

Brucsis, L. et al. "Substituionasreaktionen an 1,4-dihalogen-2,3,5,6-tetracyan-benzolen," Chem. Ber. 109(1976) pp. 2469-2474.

Cherkashin M. I. et al. "Studies on 2,4,5-triarylimidazoles," Izv. Akad. Nauk SSSR, Seriya Khim. 1982, 2, pp. 376-377.

Chonan et al. "The synthesis of difluoro and dimethyl derivatives of 2,6-bis(dicyanomethylene)-2,6-dihydro-4H-cyclopenta[2, I-b:3,4-b']-dithiophen-4-one (CPDT-TCNQ) and the Conducting Properties of the Metallic Salts Based on the Dimethy Derivative," The Chemical Society of Japan (2004) pp. 1487-1497.

Dedik, S.G. et al. "Tetrahalotetraazafulvalenes-new strong electron acceptors," Chemistry of Heterocyclic Compounds (A Translation of Khimiyageterotsiklicheskikh Soedinenii), Plenum Press Co., New York, U.S., vol. 10, Jan. 1, 1989, p. 1421.

Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.

Fatiadi et al. "Electrochemical Oxidation of Several Oxocarbon Salts in N,N-dimethylformamide," J. Electroanalytical Chem. (1982) vol. 135, pp. 193-209.

Fatiadi, "Psuedooxocarbons, Synthesis of 1,2,3-tris(dicyanomethylene)croconate Salts; A New Bond-Delocalized Dianion, Croconate Blue," J. Org. Chem. 1980, 45, 1338-1339.

Fatiadi, "Synthesis of 1,3-(dicyanomethylene)croconate Salts. New Bond-Delocalized Dianion, Croconate Violet," Journal of the American Chemical Society, Apr. 12, 1978, pp. 2586-2587.

Fausett, B.W. et al. "Palladium-catalyzed coupling of thiol esters with aryl and primary and secondary alkyl organiindium reagents," J. Org. Chem. (2005) 70(12) pp. 4851-4853.

Fenghong Li et al., "Leuco Crystal Violet as a dopant for n-doping of organic thin films of fullerene C60," J. Phys. Chem. B 2004, 108, pp. 17076-17088.

Fild, Manfred et al. "Group VA pentafluorophenyl compounds. 14. Pentafluorophenyl-substituted phosphoranes," Zeitschrift Fuer Anorganische und Allgemeine Chemie, 439, pp. 145-152 (1978).

Fukunaga, T. et al. "Negatively substituted trimethylenecyclopropane dianions," J. Am. Chem. Soc., 1976, pp. 610-613.

Gan, F. "Optical nonlinearity of hybrid and nanocomposite materials prepared by the Sol-Gel method," J. of Sol-Gel Science and Technology, 13, 559-563 (1998).

Ganzorig, C. et al., "p-Typed Semiconducts of Aromatic Diamines Doped with SbC15," Chemistry Letters 2000, pp. 1032-1033.

Gibbons, M.N. et al. "Multiply Bridged Diantimony Compounds," Phosphorus, Sulfur, & Silicon 93/94 (1994).

Giovanella, et al. "Electroluminescence from two fluorinated organic emitters embedded in polyvinyl carbazole," Applied Physics Letters, vol. 87, pp. 171910-1-3, 2010.

Glemser, O. et al. "Synthese von Tris-pentafluorphenylarsin, -stibin und -phosphin sowie von Trimethyl-pentafluor-phenylsilan," Angew. Chemie (1964) 76, 953.

Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.

Gregg, B.A. et al., "On the superlinear increase in conductivity with dopant concentration in excitonic semiconductors," Applied Physics Letters, vol. 84, No. 10, Mar. 8, 2004, pp. 1707-1709.

Gufeng, He et al., "High-efficiency and low-voltage p-i-n electrophosphorescent organic light-emitting diodes with double-emission layers," Applied Physics Letters, vol. 85, No. 17, Oct. 25, 2004, pp. 3911-3913.

Haddon, R.C. et al., "Conducting films of C60 and C70 by alkali-metal doping," Nature, vol. 350, Mar. 28, 1991, pp. 320-322.

Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.

Harris, G. S. et al. "The Reaction of Trispentafluorophenylstibine with Halogens and Interhalogens," J. Fluorine Chem. 37 (1987) pp. 247-252.

Hill, J. "Oxidative Dimerization of Benzimidazole," J. Org. Chem. 1963, 28, pp. 1931-1932.

Hopf et al. "Uber einen neuen Kohlenwasserstoff C18H24 . . . ," Helvetica Chimica Acta, vol. XLIV, Issue II (1961), No. 46, extract from p. 380-386.

Hopf et al., "Preparation and Properties, Reactions, and Applications of Radialenes," Angewandte Chemie, vol. 31, No. 8, Aug. 1992, pp. 931-954.

Iyoda, et al. "Novel synthesis of hexaaryl[3]radialenes via dibromo[3]dendralenes," Tetrahedron Letters 41 (2000), 6 pgs.

Japp, F. et al. "Constitution of Glycosine," J. Chem. Soc. Trans. 1887, 51, pp. 552-557.

Jensen, W.B.; The Generalized Lewis Acid Based Concepts, John Wiley & Sons, New York, 1980, pp. 113-195.

Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.

Katz, H.E. et al., "Pyridyl Dicyanoquinodimethane Acceptors for Electroactive Solids," J. Org. Chem. 56 (1991) pp. 5318-5324.

Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179, 2010.

Kikuchi, A et al. "A new family of pi-conjugated delocalized biradicals: electonic structures of 1,4-bis(2,5-diphenylimidazol-4-ylidene)cyclohexa-2,5-diene," J. Phys. Chem. B., 2005, 109, pp. 19448-19453.

Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.

Kimura, M. et al. "Preparation of 4-(4,5-diphenyl-1H-imidazol-2-yl)benzaldehyde and Its Practical Synthetic Use in the Synthesis of Unsymmetrically Substituted Imidazoles," ITE Letters on Batteries, New Technologies and Medicine, 2002, 3, pp. 30-34.

Klopman, G. "Chemical Reactivity and th Concept of Charge-and Frontier-controlled reactions," Journal of the American Chemical Society., vol. 90, No. 2, Jan. 17, 1968, pp. 223-234.

Koster, et al. "Synthesis and reactions of a tetraquinocyclobutane," Dept. of Chemistry, Univ. of Wisconsin, J. Org. Chem., vol. 40, No. 16, 1975, pp. 2300-2304.

Kozaki, M. et al. "Preparation, Properties, and Reduction of Heteroaromatic Quinoids with 1,4-diazacyclopentadien-2-ylidene Terminals," Org. Lett. 2005, 7, pp. 115-118.

Krebs, F.C. et al. "Superradiant properties of 4,4'-bis(1H-phenanthro[9,10-d]imidazol-2-yl)biphenyl and how a laser dye with exceptional stability can be obtained in only one synthetic step," Tetrahedron Lett. 2001, 42, pp. 6753-6757.

Lane, E.S. "A Modified Benziminazole Synthesis," J. Chem. Soc. 1953, pp. 2238-2240.

Lehmstaedt, K. et al. "Halogen-2,2'-diimidazole und ihre Umsetzungen mit Aminen zu Farbstoffen," Ber. Dt. Chem. Ges. B, 1943, pp. 879-891.

Leyden, R. et al. "Thermally Induced Degradation of 2,3,5,6-tetrachloroterephthalylidenebis(o-aminoaniline)," J. Org. Chem. 1983, 48, pp. 727-731.

Li, J. Y. et al. "Enhancement of green electroluminescence from 2,5-di-p-anisyl-isobenzofuran by double-layer doping strategy," Preparation and Characterization, vol. 446, No. 1, pp. 111-116, 2004.

Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.

Maennig, B. et al., "Organic p-i-n solar cells," App. Phys. 2004, A 79, pp. 1-14.

Matschke, M. et al. "Bis-4h-imidazoles-tetraazafulvalenes-2,2'-biimidazoles: three variations of one redox system," Tetrahedron, vol. 62, No. 36, Sep. 4, 2006, pp. 8586-8590.

Mayer, U. et al. "Uber 2,3,6,7-tetraphenyl-1,4,5,8-tetraazafulvalen," Tetrahedron Lett. 1966, 42, pp. 5221-5223.

Mayer, U. et al. "Uber Biradikale, Chinone und Semichinone der Imidazolyl-Reihe," Angew. Chem. 1966, 78, p. 303.

Minoura, M. et al. "Hexaaryltellurium, the First Neutral Compounds Comprising Hexaarylated Elements," Angew. Chem. Int. Edit. 35 (22) pp. 2660-2662 (1996).

Miyasato, M. et al. "Syntheses and Reactions of Hexavalent Organitellurium Compounds Bearing Five or Six Tellurium-Carbon Bonds," Chem.-A European J. 10(10) pp. 2590-2600 (2004).

Muramatsu, T. et al, "Visible Light Sensitive Cyclomer and Its Tautomeric Dispiro Compound Formed from Bispyridiny Diradical," J. Am. Chem. Soc. 2005, 127, 4572-3.

Muramatsu, T. et al., "Photosensitive Cyclomer Formation of 1,1'-(1,2-ethanediyl)bis(pyridinyl) diradical and its derivativese," J. Am. Chem. Soc. 1989, 111, 5782-7.

Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.

Oeter, D. et al., "Doping and Stability of Ultrapure alpha-oligothiophene Thin Films," Synthetic Metals, 61, 1993, pp. 147-150.

Okada, K. et al. "Detection of a diradical intermediate in the cis-trans isomerization of 5,5'-bis(4,5-diphenyl-2H-imidazol-2-ylidene)-5,5'-dihydro-delta 2,2'-bithiophene," Tetrahedron Lett. 2006, 47, pp. 5375-5378.

Okada, K. et al. "Novel Dimers of 2,2'-(m-Phenylene)bis(4,5-diphenyl-1-imidazolyl) Diradical," Chem. Lett. 1998, pp. 891-892.

Otero, A. et al. "Pentachlorophenyl-arsenic, -antimony and -bismuth compounds," J. of Organometallic Chemistry, vol. 171, No. 3, Jan. 1, 1979, pp. 333-336.

Otero, A. et al. "Pentafluorophenylantimony compounds," J. Organometallic Chem. 154 (1978) pp. 13-19.

Ouchi, A. et al. "13C-nuclear magnetic resonance of some triaryl- and tri-alkylantimony and -bismuth derivatives," J. of Inorganic and Nuclear Chemistry, vol. 37, Issue 11, Nov. 1975, pp. 2347-2349.

Ouchi, A. et al. "The syntheses and properties of some alkylthioacetato and arylthioacetato derivatives of triphenylantimony(V) and -bismus (V)," J. of Inorganic and Nuclear Chemistry, vol. 37, Issue 12, Dec. 1975, pp. 2559-2561.

Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.

Parthasarathy, G. et al., "Lithium doping of semiconducting organic charge transport materials," J. Appl. Phys., vol. 89, No. 9, May 1, 2001, pp. 4986-4992.

Petzhold, C. "Beitrage zur Synthese funktioneller 1,4,5,8-tetraazafulvalenen," Dissertation; Friedrich-Schiller-Universitat Jena; 2006.

Pfeiffer, M, et al., "Doped Organic semiconductors: physics and application in light emitting diodes," Organic Electronics, Elsevier, Amsterdam, NL, vol. 4, No. 2/3, Sep. 2003, pp. 89-103, XP001177135, ISSN: 1556-1199.

Rake, A. T. et al. "Pentafluorophenyl and phenyl-phosphinidene ions and their group V analogues," Oms. Organic Mass Spectrometry, vol. 3 Jan. 1, 1970, pp. 237-238.

Rasmussen, P.G. et al. "Complexes of the New Ligand Tetracyanobiimidazole," J. Am. Chem. Soc. 1982, 104, pp. 6155-6156.

Rezende, M. C. et al. "An Alternative Preparation of Bisbenzimidazoles," Syn. Comm. 2001, 31, pp. 607-613.

Rezende, M. et al. "Puzzling Formation of Bisimidazole Derivatives from Hexachloroacetone and Diamines," Tetrahedron Lett. 1996, 37, 5265-5268.

Sakaino, Y. "Structures and Chromotropic Properties of 1,4-bis(4,5-diphenylimidazol-2-yl)benzene Derivatives," J. Org. Chem. 1979, 44, pp. 1241-1244.

Sato, S. et al. "Isolation and Molecular Structure of the Organo-persulfuranes [12-S-6(C6)]," J. Am. Chem. Soc. 128(21) pp. 6778-6779 (2006).

Schmidt, "Reaktionen von Quadratsaure und Quadratsaure-Derivaten," Synthesis, Dec. 1980, extract pp. 966, 24 total pages.

Schneiders, P. et al. " Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.

Schwarz, W. M. et al., "Formation of Stable Free Radicals on Electroreduction of N-alkylpyridium salts," J. Am. Chem. Soc., 33 3164 (1961).

Seitz, G., Nachr. Chem. Tech. Lab 28 (1980), No. 11, extract pp. 804-807, total pages: 6: "Pseudooxokohlenstoffe."

Sekine, T. et al. "Dimerizations of pi-Rich N-heteroaromatic compounds and xanthine derivatives," Chem. Pharm. Bull. 1989, 37, pp. 1987-1989.

Sharma, G.D. et al., "Influence of Iodine on the Electrical and Photoelectrical Properties of Zinc Phthalocyanine Think Film Devices," Materials Science and Engineering, B41, 1996, pp. 222-227.

Singhal, K. et al. "One the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.

Smith, M.B. Organic Synthesis, McGraw-Hill, Inc. 1994, Chapter 1.

Sprenger, et al. "The cyclobutenediylium cation, a novel chromophore from squaric acid," Angew. Chem. International Edition, vol. 6 (1967), No. 6, pp. 553-554.

Suschitzky, H. "Syntheses and Reactions of 2,2'-bisbenzimidazole Systems," J. Heterocyclic Chem. 1999, 36, pp. 1001-1012.

Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.

Takahashi et al. "Novel Electron Acceptors for Organic Condcutors: 1,2-Bis(p-benzoquino)-3-[2-(dicyanomethylene)-2,5-thienoquino]cyclopropane Derivatives," J. Chem. Soc., Chem. Commun., 1994, pp. 519-520.

Takahashi et al. "Novel metallic charge-transfer complexes composed of a [3]radialene type acceptor: a 1,2-bis(p-benzoquino)-3-[2-(dicyanomethylene) . . . " Advanced Materials, July, No. 7, 3 pgs, 2010.

Vaid T.P. et al, "Investigations of the 9,10-diphenylacridyl radical as an isostructural dopant for the molecular semiconductor 9, 10-diphenylanthracene," Chemistry of Materials, American Chemical Society, Bd. 15, Nr. 22, 4292-4299 (2003).

Vyas, P.C. et al. "A simple synthesis of 2,2'-bis-benzimidazoles," Chem. Industry, 1980, pp. 287-288.

Weiss, M. "Acetic Acid-Ammonium Acetate Reactions. 2-Isoimidazoles as Intermediates in Imidazole Formation," J. Am. Chem. Soc. 1952, 74, pp. 5193-5195.

West, R. et al., "Diquinocyclopropanones, Diquinoethylenes, and the Anion-Radical and Free-Radical Intermediates in their Formation," Dept. of Chemistry, Univ. of Wisconsin, Feb. 24, 1975, pp. 2295-2299.

Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).

Yamaguchi, et al., "New Approaches to Tetracyanoquinodimethane," Bull. Chem. Soc. Jpn. 62 (1989) pp. 3036-3037.

Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.

Yoshiko, S., et al. "The Quinoid-biradical Tautomerism of 3,6-bis(4,5-diphenyl-2H-imidazol-2-ylidene)-1,4-cyclohexadiene," Nippon Kagaku Kaishi, 1972, 1, pp. 100-103.

Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).

Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.

Ziegenbein, W. "The cyclobutenediylium cation, a novel chromophore from squaric acid," Angew. Chem., 79:12, pp. 581-582 (1967).

English Translation of Japanese Office Action; Japanese Patent Application No. 2005-228491; Apr. 17, 2009.

International Search Report, International App. No. PCT/EP2007/002359, May 24, 2007.

Notice of Allowance, U.S. Appl. No. 11/196,491; Apr. 13, 2009.

Notice of Allowance, U.S. Appl. No. 11/196,491; Oct. 20, 2008.
Response to Office Action for U.S. Appl. No. 11/196,491; Aug. 11, 2008.
Final Office Action, U.S. Appl. No. 11/196,491; Feb. 11, 2008.
Response to Office Action for U.S. Appl. No. 11/196,491; Nov. 5, 2008.
Non-Final Office Action, U.S. Appl. No. 11/196,491, Jul. 3, 2007.
International Search Report and Preliminary Report on Patentability for PCT/DE2008/001080; Jul. 11, 2008.
International Search Report for PCT/DE2008/00654; Jun. 15, 2009.
International Search Report and Preliminary Report on Patentability for PCT/EP2006/010816; Feb. 9, 2007.
Advisory Action for U.S. Appl. No. 11/315,072, mailed Mar. 8, 2010.
Response to Final Office Action for U.S. Appl. No. 11/315,072; Feb. 17, 2010.
Final Rejection for U.S. Appl. No. 11/315,072; Nov. 16, 2009.
Response to Office Action for U.S. Appl. No. 11/315,072; Jul. 29, 2009.
Non-Final Rejection for U.S. Appl. No. 11/315,072; Apr. 29, 2009.
Non-Final Rejection for U.S. Appl. No. 11/315,072; Nov. 12, 2008.
Response to Office Action for U.S. Appl. No. 11/315,072; Feb. 10, 2009.
European Search Report for EP 07009366; Oct. 19, 2007.
International Search Report for PCT/EP2008/003792; Sep. 2, 2008.
Disclosure Pursuant to 37 C.F.R. 1.56 for U.S. Appl. No. 11/688,777 (submitted herewith), 2010.
Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.
Bard, A. J., Faulkner, R.J., Electrochemical Methods: Fundamentals and Applications, Wiley, 2nd Ed., 2000 (Chapter 2).
D'Andrade, B.W. et al., "Relationship between the ionization and oxidation potentials of molecular organic semiconductors," Organic Electronics 6, 2005, pp. 11-20.
Gao, W. et al., "Effect of electrical doping on molecular level alignment at organic-organic heterojunctions," Applied Physics Letters, vol. 82, No. 26, Jun. 30, 2003, pp. 4815-4817.
Harada, K. et al. "Organic Homojunction Diodes with a High Built-in Potential: Interpretation of the Current-Voltage Characteristics by a Generalized Einstein Relation," Phys. Rev. Lett. 94, 036601 (2005).
Huang, Jingsong et al., "Low-voltage organic electroluminescent devices using pin structures," Applied Physics Letters, vol. 80, No. 1, Jan. 7, 2002, pp. 139-141.
Kido, Junji et al., "Bright Organic Electroluminescent Devices Having a Metal-doped Electron-injecting Layer," Applied Physics Letters, vol. 73, No. 20, Nov. 16, 1998, pp. 2866-2868.
Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.
Miller, L.L. et al., "A simple comprehensive correlation of organic oxidation and ionization potentials," J. Org. Chem., 1972, vol. 37, No. 6, pp. 916-918.
Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.
Parker, "On the Problem of Assigning Values to Energy Changes of Electrode Reactions," Journal of the American Chemical Society, 96:17, Aug. 21, 1974, pp. 5656-5661.
Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.
R. Schlaf et al., "Homo/Lumo Alignment at PTCDA/ZnPc and PTCDA/CIInPc Heterointerfaces Determined by Combined UPS and XPS Measurements," J. Phys. Chem. B 1999, 103, pp. 2984-2992.
Tang, C.W. et al., "Organic electroluminescent diodes," Applied Physics Letters, vol. 51, No. 12, Sep. 21, 1987, pp. 913-915.
Tang, T.B. et al., "Ionization thresholds of merocyanine dyes in the solid state," Journal of Applied Physics, vol. 59, (1), Jan. 1986, pp. 5-10.
Werner, A. G. et al., "Pyronin B as a donor for n-type doping of organic thin films," Applied Physics Letters, vol. 82, No. 25, Jun. 23, 2003, pp. 4495-4497.
Yao, Fu et al., "Quantum-chemical predictions of Absolute standard redox potentials of diverse organic molecules and free radicals in acetonitrile," J. Am. Chem. Soc. 2005, 127, pp. 7227-7234.
Zhou, X. et al., "Very low operating voltage organic light-emitting diodes using a p-doped amorphous hole injection layer," Applied Physics Letters, vol. 78, No. 4, Jan. 22, 2001, pp. 410-412.
Zimmerman, T. et al. "Benzocycloalkenone und dihydro-2H, 7H-1-benzopyranone aus 2,4,6-triaryl-pyryliumsalzen und cycloalkan-1,2-dionen," J. Prakt. Chem. 331 pp. 306-318 (1989).
Non-Final Rejection for U.S. Appl. No. 12/046,620; Nov. 25, 2009.
Response to Restriction Requirement for U.S. Appl. No. 12/046,620; Aug. 24, 2009.
Restriction Requirement for U.S. Appl. No. 12/046,620; Jul. 22, 2009.

* cited by examiner

HETEROCYCLIC RADICAL OR DIRADICAL, THE DIMERS, OLIGOMERS, POLYMERS, DISPIRO COMPOUNDS AND POLYCYCLES THEREOF, THE USE THEREOF, ORGANIC SEMICONDUCTIVE MATERIAL AND ELECTRONIC OR OPTOELECTRONIC COMPONENT

CROSS-REFERENCE TO RELATED APPLICATION

Applicants hereby claim priority under 35 U.S.C. 119(a) to European Patent Application No. EP 06005687.6, filed Mar. 21, 2006 the disclosure of which is expressly incorporated herein by reference in its entirety.

The present invention relates to heterocyclic radicals or diradicals, the dimers, oligomers, polymers, dispiro compounds and polycycles thereof, to the use thereof, to organic semiconductive materials and to electronic components.

It is known to modify the electrical properties of organic semiconductors, in particular their electrical conductivity, by means of doping, as is the case also in respect of inorganic semiconductors, such as silicon semiconductors. Here, the conductivity, which is initially very low, is increased by generating charge carriers in the matrix material, and depending on the type of dopant used a change in the Fermi level of the semiconductor may also be achieved. Doping in this case leads to an increase in the conductivity of charge transport layers, as a result of which ohmic losses are reduced, and to an improved transfer of the charge carriers between the contacts and the organic layer.

The inorganic dopants used to date, such as alkali or alkaline earth metals (e.g. caesium) or Lewis acids (e.g. $FeCl_3$), are usually disadvantageous in the case of organic matrix materials on account of their high diffusion coefficient, since the function and stability of the electronic components is impaired. These inorganic dopants are also associated with difficulties in production, since they usually have a high vapour pressure at room temperature and may contaminate the production systems in vacuum processes. Alkali and alkaline earth metals in particular have the further disadvantage that use thereof is made more difficult on account of their high reactivity to air. It is also known to release dopants in the semiconductive matrix material via chemical reactions, in order to provide dopants. However, the oxidation potential of the dopants released in this way is often not sufficient for various applications, such as in particular for organic light-emitting diodes (OLEDs). Moreover, when the dopants are released, further compounds and/or atoms are also generated, for example atomic hydrogen, as a result of which the properties of the doped layer and of the corresponding electronic component are impaired.

Furthermore, compounds used as dopants often do not have a sufficiently low ionisation potential for the respective application.

The object of the present invention is to provide novel compounds which can be used as n-dopants, as an injection layer or as a blocking layer, wherein the compounds also have sufficiently low oxidation potentials for producing electron transport materials for organic light-emitting diodes, without having any disruptive effect on the matrix material, and are intended to provide an effective increase in the number of charge carriers in the matrix material and are relatively easy to handle.

Further objects of the present invention consist in specifying possible uses of these compounds, in providing organic semiconductive materials and an electronic component or optoelectronic component in which the compounds can be used, e.g. in photoinitiated memories.

The first object is achieved by the heterocyclic radicals or diradicals, the dimers, oligomers, polymers, dispiro compounds and polycycles thereof, which are described herein. The heterocyclic radicals or diradicals, the dimers, oligomers, polymers, dispiro compounds and polycycles thereof, have structures according to the following formulae:

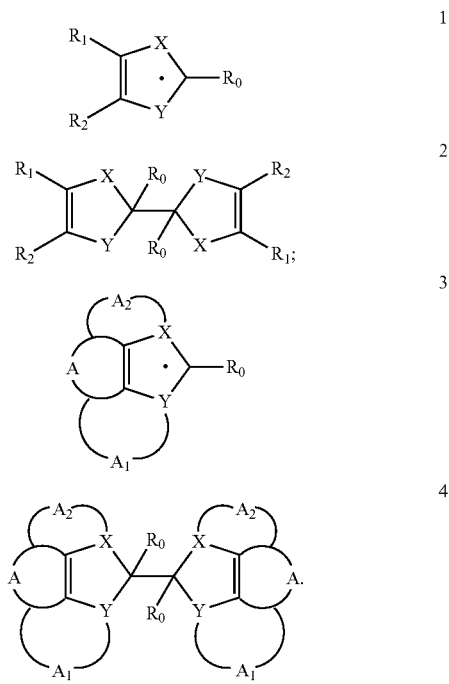

wherein structures 3 and 4 have one or more cyclic linkages A and/or $A_1$ and/or $A_2$, wherein A, $A_1$ and $A_2$ may be carbocyclic, heterocyclic and/or polycyclic ring systems, which may be substituted or unsubstituted;

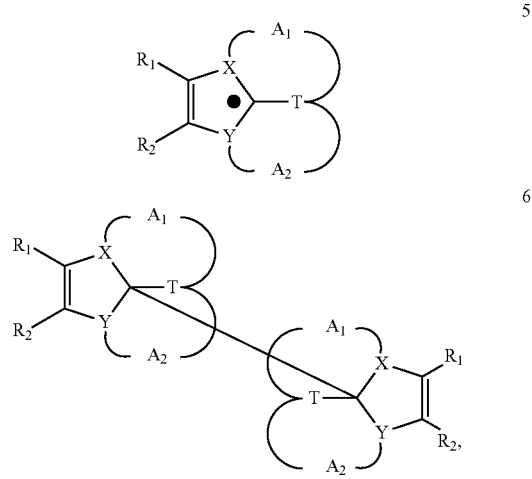

wherein $A_1$ and $A_2$ may be present individually or together and $A_1$ and $A_2$ are as defined for structures 3 and 4 and $T=CR_{22}$, $CR_{22}R_{23}$, N, $NR_{21}$, O or S;

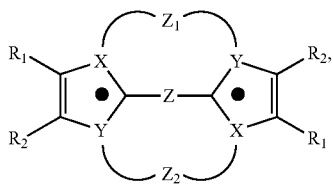

wherein structure 7 has one or more bridge bonds Z and/or $Z_1$ and/or $Z_2$, and Z, $Z_1$ and $Z_2$ may independently be selected from alkyl, alkenyl, alkenyl, cycloalkyl, sililyl; alkylsililyl, diazo, disulphide, heterocycloalkyl, heterocyclyl, piperazinyl, dialkyl ether, polyether, primary alkylamine, arylamine and polyamine, aryl and heteroaryl;

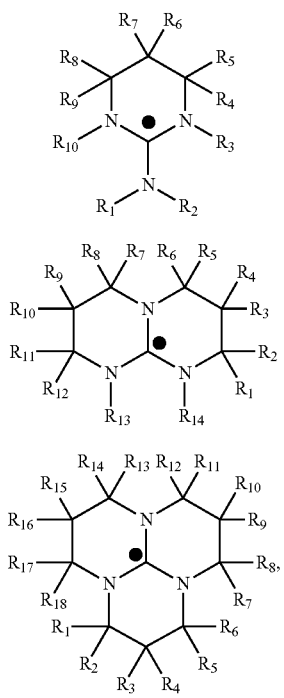

wherein in structures 8a-8c the ring size of each heterocycle may vary from 5-7 atoms: wherein X, Y=O, S, N, $NR_{21}$, P or $PR_{21}$; $R_{0-19}$, $R_{21}$, $R_{22}$ and $R_{23}$ are independently selected from, substituted or unsubstituted, aryl, heteroaryl, heterocyclyl, diarylamine, diheteroarylamine, dialkylamine, heteroarylalkylamine, arylalkylamine, H, F, cycloalkyl, halocycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl and trialkylsilylalkynyl, or $R_{0-19}$, $R^{21}$, $R_{22}$ and $R_{23}$, alone or in combination, form part of a (hetero)aliphatic or (hetero)aromatic ring system;

with the proviso that the following structures are excluded: structure 3a

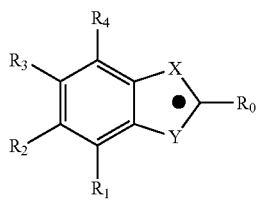

where $R_1$-$R_4$=H, X=$NCH_3$, Y=$NCH_3$ and $R_0$=methyl;

structure 3a

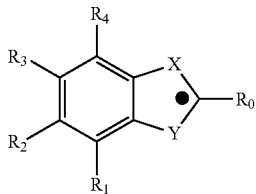

where X=$NCH_3$, Y=S and $R_0$=methyl, ethyl, butyl, phenyl, 4-tolyl, 4-anisyl, 4-chlorophenyl;

structure 1

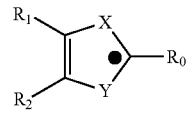

where X=$NR_{21}$, Y=$NR_{22}$ and $R_{1,2,21,22}$=phenyl, 4-tolyl and/or 4-anisyl, $R_0$=phenyl, 4-tolyl or 4-anisyl.

More preferably are compounds having the following structure:

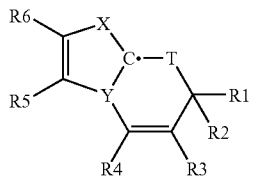

5e

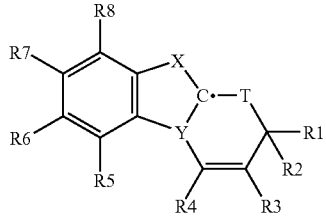

5f

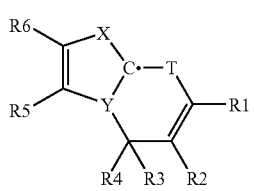

5g

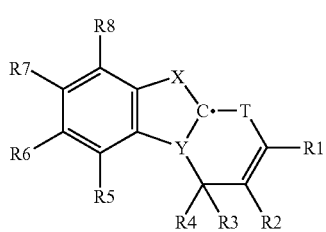

5h

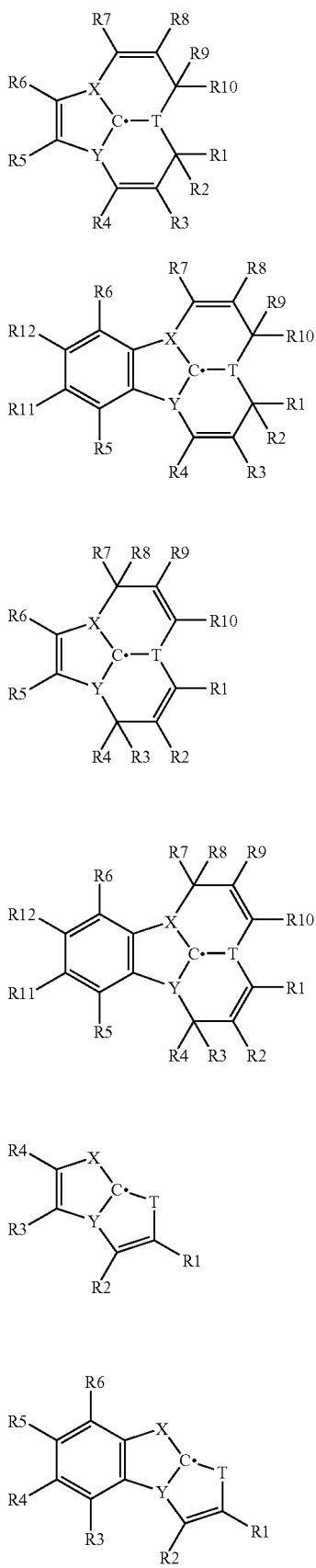

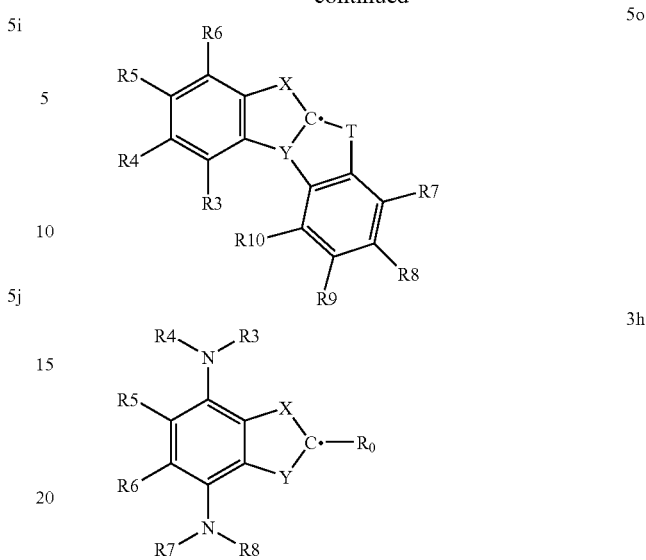

$R_0$, $R_1$-$R_{12}$ in structures 5e-5o and 3h can be chosen from the definition for the R's described herein.

Further, structure 5c is preferred with $R_1$-$R_{16}$=H or $R_1$, $R_4$-$R_{16}$=H and $R_2$, $R_3$=$CH_3$.

Additionally a particularly preferred compound is based on structure 1a with Y=$NR_{21}$ with $R_{21}$=alkyl, preferably methyl; with $R_0$, $R_{21}$=alkyl, preferably methyl; $R_1$, $R_2$=aryl, especially phenyl, tolyl, xylyl, anisyl, thienyl, furanyl, alkyl, especially cyclohexyl, cyclopentyl, n-alkyl; or mixed variations with $R_1$=alkyl, especially methyl, ethyl, propyl, and $R_2$=aryl, especially phenyl, tolyl, xylyl, anisyl, thienyl, furanyl.

Within the context of the present invention, the term "dimers" is understood to mean compounds which occur by reacting two monoradicals or diradicals with each other.

The term "oligomers" is understood to mean compounds which are composed of a plurality of diradicals, wherein a first radical end of a diradical reacts with a first end of a further diradical and a second end of the newly formed, larger diradical in turn reacts with a second further diradical. The ends of such oligomers can be reacted with monoradicals.

The term "polymer" is understood to mean compounds which, compared to oligomers, are composed of a larger number of diradicals.

A "dispiro compound" is according to the present invention an intramolecular addition product of a diradical, the radical centers of which are separated by a structural element of that kind, that said structural element connects the radical bearing carbon atoms, i.e. the carbon atoms which add to each other.

The term "polycycle" is meant to comprise an intramolecular addition product of a diradical, the radical centers of which are separated by a structural element of that kind that said structural element connects at least one other carbon atom than the ones bearing radicals (e.g. at least one atom in alpha position).

The radicals $R_{0-19}$, $R_{21}$, $R_{22}$ and $R_{23}$ may preferably be substituted aryl, wherein the substituents are preferably electron-donating radicals, for example dialkylamine, julolidyl, diarylamine, alkylarylamino, diheterocyclylamine, diheteroalkylamine, alkoxy, aryloxy, alkylmercaptyl, arylmercaptyl, alkyl, sililyl, haloalkyl, cycloalkyl, halocycloalkyl, alkenyl, alkynyl, trialkylsililylalkynyl or styryl.

All the claimed compounds may be perfluorinated or partially perfluorinated, in particular saturated bridges and handles.

It has surprisingly been found that a much stronger and/or more stable dopant than is the case with previously known donor compounds is obtained if free radicals and diradicals, the dimers, oligomers, dispiro compounds or polycycles thereof are used in neutral form as an n-dopant for an organic semiconductive matrix material. In particular, when using the compounds according to the invention as an n-dopant, the conductivity of charge transport layers can be significantly increased and/or the transfer of the charge carriers between the contacts and the organic layer can be significantly improved in applications as an electronic component. The compounds according to the invention themselves can also be used as transport materials. The concentration ratios during the vapour deposition process to produce the organic semiconductive material can therefore be 10:1 for example between the radical (or dimer) and conventional matrix materials.

Without being restricted thereby, it is assumed that when, according to the invention, the disclosed heterocyclic compounds are used in a doped layer, the cations associated with the respective heterocyclic radicals and diradicals are formed, in particular by the transfer of at least one electron from the respective heterocyclic radical or diradical, its dimer, oligomer, dispiro compound or polycycle, to the surrounding matrix material. In the process, anions of the matrix material are also formed, which can move on the matrix material. In this way, the matrix material obtains a conductivity which is increased in comparison to the conductivity of the undoped matrix material. Conductivities of undoped matrix materials are generally $<10^{-8}$ S/cm, in particular often $<10^{-10}$ S/cm. It should be ensured that the matrix materials have a sufficiently high purity. Such purities can be achieved using conventional methods, for example gradient sublimation. By doping, the conductivity of such matrix materials can be increased to more than $10^{-8}$ S/cm, often $>10^{-6}$ S/cm. This applies in particular to matrix materials which have a reduction potential of less than $-1$ V vs. Fc/Fc$^+$, preferably less than $-1.7$ V vs. Fc/Fc$^+$, in particular less than $-2.1$ V vs. Fc/Fc$^+$. The notation Fc/Fc$^+$ relates to the redox pair ferrocene/ferrocenium, which is used as reference in an electrochemical potential determination, for example cyclic voltammetry.

In the present application, a dopant is understood to mean on the one hand a material which is mixed in ("the layer is doped with the dopant"). On the other hand, the dopant may be the redox-active species which brings about charge transfer conductivity ("the dopant brings about n-doping"). It is assumed that the dimers, etc. are dopants of the first type, whereas the corresponding radicals are dopants of the second type.

It has also been found according to the invention that the heterocyclic radicals or diradicals and the derivatives thereof can be used as an injection layer in electronic components, preferably between an electrode and a semiconductor layer, which may also be doped, or also as a blocking layer, preferably between an emitter layer and a transport layer, or as a semiconductor layer in electronic components. It has furthermore been found that a photo-induced or light-induced irreversible doping of organic semiconductors is possible by means of the compounds according to the invention, in particular the generation of said radicals and diradicals by cleaving their dimers or oligomers or dispiro compounds by means of electromagnetic radiation and subsequent irreversible doping of n-conductive semiconductors.

It is also conceivable to use the compounds according to the invention as radical scavengers or antioxidants in food chemistry, pharmacy, in fire-fighting or as pesticides, in particular as an insecticide, herbicide, fungicide or the like. The use as radical initiators for radical reactions (preferably radically induced polymerisations or living radical polymerisations) is also conceivable. Finally, it should be mentioned that triplet diradicals can also be used as a magnetic compound in the form of memory or switch structures in organic electronic and optoelectronic components.

Coming back to the preferred use of the inventive heterocyclic radicals, diradicals and derivatives thereof as a dopant, the doping may take place in a light-induced manner for example by means of the following three mechanisms:

1. The dimer/oligomer/polymer/dispiro compound or polycycle itself absorbs electromagnetic radiation of suitable wavelength and is thereby cleaved into the doping radicals or diradicals. An electron is transferred from the HOMO of the radical/diradical to the LUMO of the matrix material.

2. The matrix material is excited by exposure to electromagnetic radiation, so that an electron from the HOMO of the dopant (dimer/oligomer/polymer/dispiro compound/polycycle) is transferred to the former HOMO, which is now single-occupied. The dopant then undergoes an irreversible reaction.

3. The dopant (dimer/oligomer/polymer/dispiro compound/polycycle) is excited photochemically, then an electron transfer takes place from the single-occupied LUMO of the dopant to the LUMO of the matrix material. The dopant then undergoes an irreversible reaction.

However, it is also possible for various mechanisms to occur at the same time, and finally the electron transfer may be brought about by means of a different mechanism not mentioned here, for example by means of thermal splitting of the bond. Once the electromagnetic radiation source has been switched off, however, all or part of the conductivity is irreversibly and permanently retained.

Further objects and advantages of the compounds according to the invention will now be described on the basis of the following examples, which must be considered only by way of illustration and are no way intended to restrict the scope of the invention.

The dopants according to the invention have a surprisingly high stability with regard to their reactivity with the atmosphere.

Synthesis Methods

The radicals, diradicals and derivatives thereof according to the invention can be synthesised by known methods. It will be understood that the cited literature is mentioned only by way of example.

A complete way of obtaining the radicals/diradicals is shown schematically for all the stated compounds using the example of the benzimidazoles.

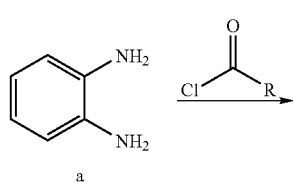

a

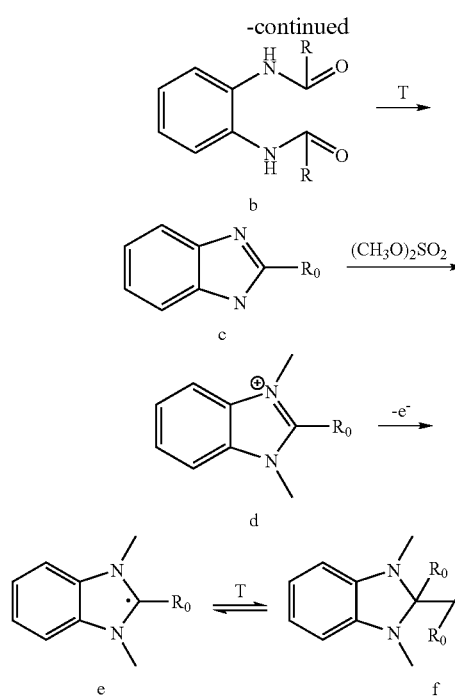

Benzimidazoles c can inter alia be easily synthesised from o-phenylenediamine a and appropriate carboxylic acid derivatives (M. R. DeLuca, S. M. Kerwin *Tetrahedron* 1997, 53 457-64) or aldehydes (M. Curini et at. *Synlett* 2004, 10, 1832-4). See also: M. R. Grimmett "Imidazole and Benzimidazole Synthesis" Academic Press; Harcourt Brace & Company, Publishers, London, San Diego, New York, Boston. o-Phenylenediamines are commercially available or can be obtained for example by the method of Suschitsky et al. (*J. Chem. Soc. Chem. Comm.* 1977, 189-90). Benzothia derivatives or oxazole derivatives can be obtained in the same way via o-mercapto- or o-hydroxyanilines. The alkylation of the N-atom(s) in the heterocyclic five-membered rings c takes place with dimethyl sulphate or diethyl sulphate in the presence of bases (H. Quast, E. Schmitt *Chem. Ber.* 1968, 101, 4012-14) or with alkyl halides. The corresponding cationic products (heteroarenium compounds) d can be isolated in neutral form e.g. as perchlorate, tetrafluoroborate, halide, tetraphenylborate or hexafluorophosphate or with other suitable counterions.

Said radicals can be prepared chemically by means of alkali metals or electrochemically or photochemically from the corresponding heteroaromatic cations by reduction (T. Muramatsu et al. *Chemistry Letters* 1996, 151-2; Pragst et al. *J. Electroanal. Chem.* 1984, 180, 141-56, J. Heinze, H. Baumgärtel, Ber. Bunsenges. 1972 76/2 94)

However, the radically usually quickly react further to form dimers f, oligomers, polymers, dispiro compounds i or polycycles (tricycles) l. The fact that radicals actually occur as intermediate stages can be detected by means of ESR spectroscopy.

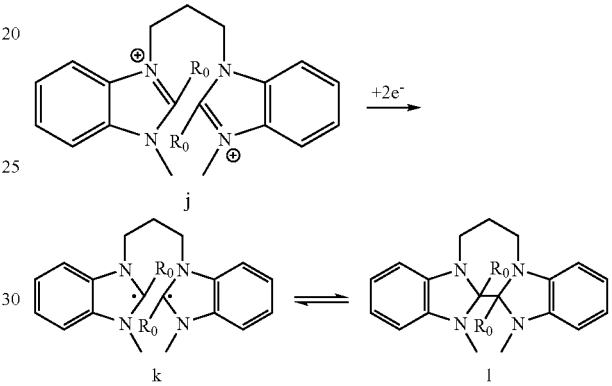

Bis-[3-methyl-2-alkyl-1,2-dihydrobenzothiazolyl-(2)] and bis-[3-methyl-2-aryl-1,2-dihydrobenzothiazolyl-(2)] compounds can be obtained directly via benzothiazolium salts and suitable Grignard compounds /A. Kinya; S, Hiroaki; I. Naoki; Bull. Chem. Soc. Japan 1979 52/1, 156-9.

Dispiro compounds i can be formed from 2,2'-bridged benzimidazoles.

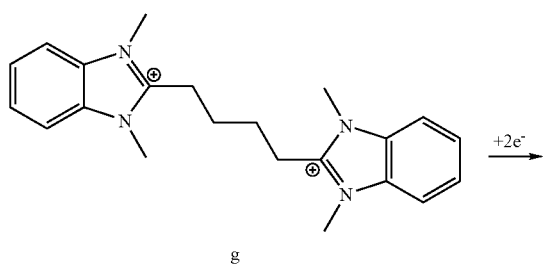

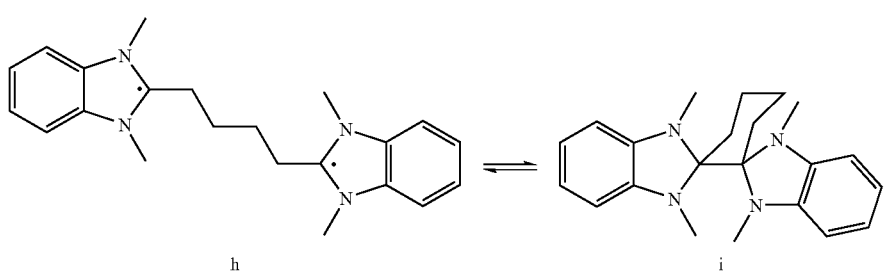

Obtaining the N-substituted Heteroaromatic Cations

EXAMPLE 1

2-Methylmercapto-1,3-dimethylbenzimidazolium perchlorate

Suspend 0.1 mol of 2-mercaptobenzimidazole in 70 ml of water. Add 0.3 mol of $NaHCO_3$ and 0.5 mol of dimethyl sulphate and stir overnight at room temperature. 12 ml of 50% tetrafluoroboric acid are added dropwise to the clear solution, which is cooled and the precipitate is removed by suction and recrystallised from 1,2-dichlorethane.
Fp.=160-3° C.

EXAMPLE 2

2-Piperidyl-1,3-dimethylbenzimidazolium perchlorate

Heat 0.01 mol of 2-methylmercapto-1,3-dimethylbenzimidazolium perchlorate with 0.01 mol of piperidine for 4 h at reflux in 250 ml of dioxane. Remove the solids by suction and recrystallise from ethanol.
Fp. 179° C.

EXAMPLE 3

2-Dimethylaminobenzimidazolium chloride

Stir 0.05 mol of o-phenylenediaminium dichloride and 0.05 mol of dichloromethylene-N,N-dimethylimmonium chloride in 100 ml of dioxane at room temperature for 12 h. Then heat at reflux for 2.5-3 h, remove the solids by suction and wash with ether. Recrystallise from ethanol.
Fp. 293° C.

EXAMPLE 4

1,4-Bis-1',1'',3',3''-tetramethylbenzimidazoium-2',2''-butane

Suspend 0.01 mol of 1,4-bisbenzimidazolyl-2',2''-butane in 30 ml of a mixture consisting of 50% water and 50% glycol monomethyl ether, add 0.06 mol of sodium hydrogen carbonate and 0.05 mol dimethyl sulphate and stir overnight at room temperature. Then filter and precipitate with 10 ml of concentrated perchloric acid.

EXAMPLE 5

2,3,5,6-Tetrahydro-1H,4H-3a,10b-diaza-6a-azoniafluoranthene

Heat 0.1 mol of 2-aminobenzimidazole with 0.2 mol of 1,3-dibromopropane and 0.3 mol of $KCO_3$ in 250 ml of DMF for 8 h at 120° C. Remove the solids by suction and fully concentrate the solvent and take up in methanol and then add 70% perchloric acid. Wash the precipitated white crystals with methanol, water and again with methanol.
Fp.: 242° C.

EXAMPLE 6

2-Isopropyl-1,3-dimethylimidazolium perchlorate

Suspend 0,1 mol of 2-mercaptobenzimidazole in 70 ml of water. Add 0.3 mol of $NaHCO_3$ and 0.5 mol of dimethyl sulphate and stir overnight at room temperature. 10 ml of 70% perchloric acid are added dropwise to the clear solution, which is cooled and the precipitate is removed by suction and recrystallised from ethanol.
Fp.=346° C.

EXAMPLE 7

Bis-(N,N',2,2'-tetramethyl-1H-benzimidazolylium)-1,3-propane diiodide

Suspend 0.02 mol of NaH under argon in 20 ml of dimethoxyethane and add 0.02 mol of 2-methylbenzimidazole under ice cooling. Once evolution of gases is complete, continue stirring for a further 60 min at room temperature and add dropwise 0.01 mol of 1,3-dibromopropane and stir for 10 min. Heat the reaction mixture at 60° C. on the water bath for 4.5 h, stir overnight at room temperature and pour onto ice/water Remove the precipitated raw product by suction and dry in vacuo. Place 0.005 mol of this intermediate product in 30 ml of water, add 0.015 mol of $NaHCO_3$ and 0.015 mol of dimethyl sulphate, stir overnight and precipitate with 1-2 ml of concentrated hydrioic acid.
Fp.: decomp.>306° C.

EXAMPLE 8

1,2,3,5,6,7-Hexamethylbenzo-1,7-dihydrobenzo[1,2-d,4,5-d']diimidazolium diperchlorate Suspend 0.013 mol of 2,6-dimethylbenzo-1,7-dihydrobenzo[1,2-d,4,5-d']diimidazole in approx. 40-50 ml of water and add 0.078 mol of $NaHCO_3$ and 0.064 mol of dimethyl sulphate. Stir for 12 h at room temperature and add dropwise 4-5 ml of 70% perchloric acid. Remove the white precipitate by suction and wash with ethanol, water and again with ethanol.
Fp.:>350° C.

Obtaining the Radicals, Diradicals and the Dimers or Oligomers and also Dispiro Compounds or Polycycles Thereof

EXAMPLE a

Bis-[1,3-dimethyl-2-N-piperidinyl-1,2-dihydrobenzimidazolyl-(2)]

Heat at reflux 0.01 mol of 2-N-piperidinyl-1,3-dimethylbenzimidazolium tetrafluoroborate with potassium in THF, filter, concentrate and cool. Remove the precipitated crystals by suction and wash with cold acetonitrile.
Fp.: 195° C.

EXAMPLE b

Bis-[1,3-dimethyl-2-isopropyl-1,2-dihydrobenz imidazolyl-(2)]

Dissolve 1,3-dimethyl-2-isopropylbenzimidazolium perchlorate in 0.1 M tetrabutylammonium perchlorate in acetonitrile and precipitate in a three-chamber electrolysis cell at −2.3 V using a mercury electrode. The white precipitate is removed by suction, washed with acetonitrile and dried in vacuo.
Fp.: 146° C.

EXAMPLE c

Bis-[1,3-dimethyl-2-N-pyrrolidyl-1,2-dihydrobenzimidazolyl-(2)]

Dissolve 1,3-dimethyl-2-N-pyrrolidylbenzimidazolium perchlorate in 0.1 M tetrabutylammonium perchlorate/DMF and precipitate in a three-chamber electrolysis cell at −2.3 V using a mercury electrode. The white precipitate is removed by suction, washed with acetonitrile and dried in vacuo.
Fp.: 120° C.

EXAMPLE d

Bis-[1,3,5,6-tetramethyl-2-isopropyl-1,2-dihydrobenzimidazolyl-(2)]

Heat at reflux 0.01 mol of 1,3,5,6-tetramethyl-2-isopropylbenzimidazolium tetrafluoroborate with potassium in THF, filter, concentrate and cool. Remove the precipitated crystals by suction and wash with cold acetonitrile.
or
Dissolve 1,3,5,6-tetramethyl-2-isopropylbenzimidazolium perchlorate in 0.1 M tetrabutylammonium perchlorate/DMF and precipitate in a three-chamber electrolysis cell at −2.3 V using a mercury electrode. The white precipitate is removed by suction, washed with acetonitrile and dried in vacuo.
Fp.: 129-30° C.

EXAMPLE e

2-Isopropyl-1,3-dimethyl-2,3,6,7-tetrahydro-1H-5,8-dioxa-1,3-diazacyclopenta[b]naphthene Dissolve 0.1 M tetrabutylammonium perchlorate/acetonitrile and precipitate in a three-chamber electrolysis cell at −2.4 V using a mercury electrode. The white precipitate is removed by suction, washed with acetonitrile and dried in vacuo.
Fp.: 142° C.

EXAMPLE f 1,2,3,5,6,7-Hexamethylbenzo-1,7-dihydrobenzo[1,2-d,4,5-d']diimidazolyl-(2) oligomeric diradical Dissolve 0.01 mol of 1,2,3,5,6,7-hexamethylbenzo-1,7-dihydrobenzo[1,2-d,4,5-d']-diimidazolium diperchlorate in 0.1 M tetrabutylammonium perchlorate/DMF and precipitate in a three-chamber electrolysis cell at −2.3 V using a mercury electrode. The white precipitate is removed by suction, washed with acetonitrile and dried in vacuo.
F.:>250° C.

EXAMPLE g

Bis-[1,3-dimethyl-2-isopropyl-1,2,4,5,6,7-hexahydrobenzimidazolyl-(2)]

Dissolve 1,3-dimethyl-2-isopropyl-4,5,6,7-tetrahydrobenzimidazolium hexafluorophosphate in 0.1 M tetrabutylammonium hexafluoro phosphate in DMF and precipitate in a three-chamber electrolysis cell at −2.6 V using a mercury electrode. The white precipitate is removed by suction, washed with acetonitrile and dried in vacuo.
Fp.: 127-9° C.

EXAMPLE h

Bis-[4,5-diphenyl-2-isopropyl-1,2-dihydroimidazolyl-(2)]

Dissolve 4,5-diphenyl-2-isopropylimidazolium hexafluorophosphate in 0.1 M tetrabutylammonium hexafluorophosphate in DMF and precipitate in a three-chamber electrolysis cell at −2.45 V using a mercury electrode. The white precipitate is removed by suction, washed with acetonitrile and dried in vacuo.
Fp.: 160-3° C.

EXAMPLE i

Bis-[3-benzyl-2-isopropyl-1,2-dihydrobenzothiazolyl-(2)]

Dissolve 3-benzyl-2-isopropylbenzothiazolium perchlorate in 0.1 M tetrabutylammonium perchlorate in acetonitrile and precipitate in a three-chamber electrolysis cell at −2.3 V using a mercury electrode. The white precipitate is removed by suction, washed with acetonitrile and dried in vacuo.
Fp.: 146° C.

Doping

Matrix Materials

As n-dopable matrix materials, use may be made inter alia of quinolinato complexes, for example of aluminum or of other main group metals, wherein the quinolinato ligand may also be substituted. In particular, the matrix material may be tris(8-hydroxyquinolinato) aluminum. Other aluminum complexes with O and/or N donor atoms may also optionally be used. Common matrix materials are also zinc phthalocyanine (ZnPc) or zinc tetraphenylporphyrin (ZnTPP), to name just a few examples of phthalocyanine or porphyrin complexes.

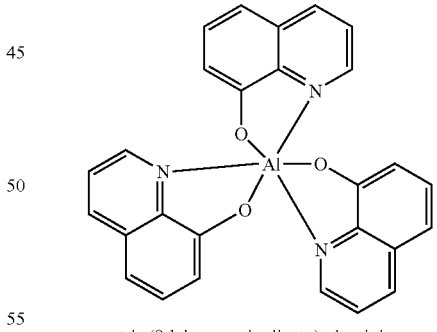

tris (8-hdroxy-quinolinato)-aluminium

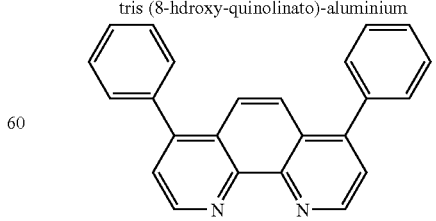

BPhen = bathophenanthroline
(4,7-Diphenyl-1,10-phenanthroline)
C24H16N2

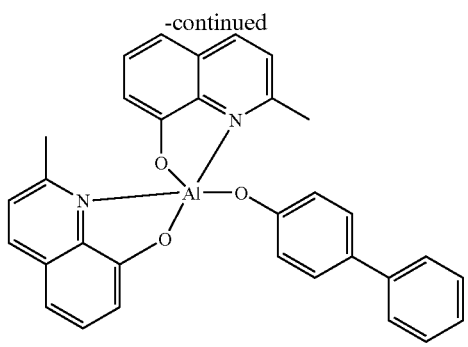

Bis-(2-methyl-8-quinolinolato)-4-(phenyl-phenolato)-aluminium-(III)

The quinolinato complexes may contain for example one, two or three quinolinato ligands, wherein the other ligands preferably complex with O and/or N donor atoms to the central atom, such as the above Al complex for example.

As the matrix material, it is also possible to use phenanthrolines, which may be substituted or unsubstituted, in particular aryl-substituted, for example phenyl- or naphthyl-substituted. In particular, Bphen can be used as matrix material.

As the matrix material, it is also possible to use heteroatoms, such as in particular triazoles, possibly also pyrroles, imidazoles, triazoles, pyridines, pyrimidines, pyridazines, quinoxalines, pyrazino-quinoxalines and the like. The heteroatoms are preferably substituted, in particular aryl-substituted, for example phenyl- or naphthyl-substituted. In particular, the following triazole can be used as matrix material. Further matrix materials can be found for example in A. P. Kulkarni et al., Chem. Mater. 16, 4556ff. (2004).

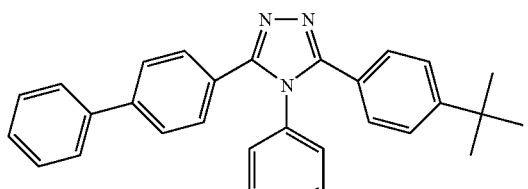

3-(4-Biphenylyl)-4-phenyl-5-tert-butylphenyl-1,2,4-triazole
C30H27N3

The matrix material used preferably consists entirely of a metallophthalocyanine complex, in particular ZnPc, a porphyrin complex, or a Buckminsterfullerene, in particular Fullerene C60.

It will be understood that, within the context of the invention, said matrix materials can also be used in a mixture with one another or with other materials. It will be understood that it is also possible to use suitable other organic matrix materials which have semiconductive properties.

Doping Method

During the doping process, the polymeric, oligomeric or dimeric compounds or dispiro compounds decompose as a result of ring opening to give the actual doping radicals. The decomposition of the polymers, oligomers and dimers and dispiro compounds may also proceed in a light-induced manner before, during or after the production of the mixed layer, and therefore exposure of the semiconductor layer to electromagnetic radiation, preferably to ultraviolet and/or visible light, advantageously takes place before, during or after the mixed vapour deposition (mixture consisting of dopant and matrix). Furthermore, exposure to heat during the vapour deposition may give rise to cleavage of the polymers, oligomers and dimers or dispiro compounds into radicals with doping properties. It may also be advantageous for some applications to heat the mixed layer during or after production.

The doping of the respective matrix material with the compounds according to the invention may be carried out by one or a combination of the following methods.
a) Mixed vapour deposition in vacuo with one source for the matrix material and one for the dopant.
b) Sequential deposition of the matrix material and of the n-dopant onto a substrate with subsequent inward diffusion of the dopant, in particular by means of a heat treatment
c) Doping of a matrix layer with a solution of n-dopant, followed by evaporation of the solvent, in particular by means of a heat treatment
d) Surface-doping of a matrix material layer by means of a layer of dopant applied to the surface.
e) Preparation of a solution of matrix molecules and dopant and subsequent production of a layer consisting of this solution by means of conventional methods such as evaporation of the solvent or spin coating.

The doping may also take place in such a way that the dopant is evaporated out of a precursor compound, which releases the dopant when heated and/or exposed to radiation. As the precursor compound, it is possible to use for example a carbonyl compound, dinitrogen compound or the like which gives off CO, nitrogen or the like when releasing the dopant wherein it is also possible to use other suitable precursors, such as salts, e.g. halides, hydrogenated compounds or the like. The exposure to radiation may take place by means of electromagnetic radiation, in particular visible light, UV light or IR light, for example laser light, or else by means of other types of radiation. The exposure to radiation may substantially provide the heat required for evaporation, and it is also possible to introduce the radiation in a targeted manner into certain bands of the compounds or precursors or compound complexes to be evaporated, such as charge transfer complexes, in order to facilitate the evaporation of the compounds by dissociating the complexes for example by transferring them into excited states. However, the complex may in particular also be sufficiently stable to be evaporated without dissociation or to be applied to the substrate under the given conditions, It will be understood that other suitable methods can also be used to carry out the doping.

In this way, according to the invention, n-doped layers of organic semiconductors can thus be produced which can be used in many ways.

DOPING USE EXAMPLES

A radical according to the invention or the oligomer, preferably dimer, thereof and diradicals or dispiro compounds and tricycles thereof are provided.

EXAMPLE I

The neutral dimer bis-[1,3-diethyl-2-methyl-1,2-dihydrobenzimidazolyl-(2)] was used together with the matrix material zinc phthalocyanine ZnPc. Doped layers with a doping ratio dopant:matrix material of 1:20 were produced by mixed vapour deposition of matrix and dopant with ZnPc as matrix material. The conductivity here is $3 \times 10^{-4}$ S/cm.

EXAMPLE II

In a manner analogous to Example I, mixed vapour deposition of bis-[1,3-dimethyl-2-isopropyl-1,2-dihydrobenzimidazolyl-(2)] and ZnPc was carried out in the ratio as given in example I. The resulting conductivity was $10^{-3}$ S/cm.

EXAMPLE III

In a manner analogous to Example I, mixed vapour deposition of bis-[1,3-dimethyl-2-isopropyl-1,2-dihydrobenzimidazolyl-(2)] and ZnTTP was carried out in the ratio as given in example I. The resulting conductivity was $10^{-8}$ S/cm.

EXAMPLE IV

In a manner analogous to Example I, mixed vapour deposition of bis-[1,3-dimethyl-2-ethyl-1,2-dihydrobenzimidazolyl-(2)] and ZnPc was carried out in the ratio as given in example I. The resulting conductivity was $10^{-4}$ S/cm.

EXAMPLE V

In a manner analogous to Example I, mixed vapour deposition of bis-[1,3-dimethyl-2-N-pyrrolidyl-1,2-dihydrobenzimidazolyl-(2)] and ZnTPP was carried out in the ratio as given in example I. The resulting conductivity was $10^{-4}$ S/cm.

EXAMPLE VI

In a manner analogous to Example I, mixed vapour deposition of bis-[1,3,5,6-tetramethyl-2-isopropyl-1,2-dihydrobenzimidazolyl-(2)] and zinc octaethylporphyrin ZnOEP was carried out in the ratio as given in example I. The resulting conductivity was $5 \times 10^{-8}$ S/cm.

EXAMPLE VII

In a manner analogous to Example I, mixed vapour deposition of 2-isopropyl-1,3-dimethyl-2,3,6,7-tetrahydro-1H-5,8-dioxa-1,3-diazacyclopenta[b]naphthene and ZnTPP was carried out in the ratio as given in example I. The resulting conductivity was $1.8 \times 10^{-4}$ S/cm.

EXAMPLE VIII

In a manner analogous to Example I, mixed vapour deposition of 2-isopropyl-1,3-dimethyl-2,3,6,7-tetrahydro-1H-5,8-dioxa-1,3-diazacyclopenta[b]naphthene and ZnOEP was carried out in the ratio as given in example I. The resulting conductivity was $5 \times 10^{-8}$ S/cm.

EXAMPLE IX

In a manner analogous to Example I, mixed vapour deposition of 2-isopropyl-1,3-dimethyl-2,3,6,7-tetrahydro-1H-5,8-dioxa-1,3-diazacyclopenta[b]naphthene and ZnPc was carried out in the ratio as given in example I. The resulting conductivity was $2.2 \times 10^{-8}$ S/cm.

EXAMPLE X

In a manner analogous to Example I, mixed vapour deposition of bis-[1,3-dimethyl-2-isopropyl-1,2-dihydroimidazolyl-(2)] and ZnPc was carried out in the ratio as given in example I. The resulting conductivity was $10^{-3}$ S/cm.

EXAMPLE XI

In a manner analogous to Example I, mixed vapour deposition of bis-[1,3-diethyl-2-methyl-1,2-dihydrobenzthiazolyl-(2)] and ZnPc was carried out in the ratio as given in example I. The resulting conductivity was $3.8 \times 10^{-7}$ S/cm.

The features of the invention which are disclosed in the above description and in the claims may be essential both individually and in any combination with one another for an implementation of the invention in its various embodiments.

The invention claimed is:

1. A heterocyclic compound, or a dimer, oligomer, polymer, dispiro compound, or polycycle thereof, having a structure according to the following formula:

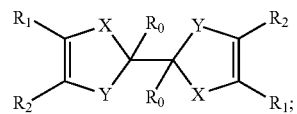

wherein X and Y are $NR_{21}$; and wherein $R_{0-2}$ and $R_{21}$ are independently selected from the group consisting of, substituted or unsubstituted, aryl, heteroaryl, heterocyclyl, diarylamine, diheteroarylamine, dialkylamine, heteroarylalkylamine, arylalkylamine, H, F, cycloalkyl, halocycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, and trialkylsilylalkynyl; or wherein $R_{0-2}$, and $R_{21}$, alone or in combination, form part of a (hetero)aliphatic or (hetero)aromatic ring system.

2. The heterocyclic compound, or the dimer, oligomer, polymer, dispiro compound, or polycycle thereof according to claim 1, wherein and $R_{0-2}$ and $R_{21}$ are selected from the group consisting of, substituted or unsubstituted, phenyl, biphenyl, naphthyl, anthranyl, thienyl, imidazolyl, pyrrolyl, thiazolyl, oxazolyl, thiadiazolyl, piperidyl, pyrrolidyl, morpholyl, and thiomorpholyl.

3. The heterocyclic compound, or the dimer, oligomer, polymer, dispiro compound, or polycycle thereof according to claim 1, wherein $R_{0-2}$ and $R_{21}$ are selected from the group consisting of alkyl, cycloalkyl, dialkylamine, diarylamine, alkoxy, aryloxy, thioalkoxy, and perfluoroalkyl.

4. An electronic or optoelectronic component comprising a heterocyclic compound, or a dimer, oligomer, polymer, dispiro compound, or polycycle thereof, wherein the heterocyclic compound, or the dimer, oligomer, polymer, dispiro compound, or polycycle thereof is a dopant for doping an organic semiconductive matrix material, a blocking layer, a charge injection layer, an electrode material, a memory material, or a semiconductor layer, and wherein the heterocyclic compound, or the dimer, oligomer, polymer, dispiro compound, or polycycle thereof, has a structure according to the following formula:

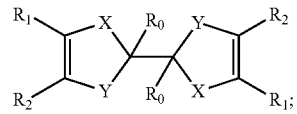

wherein X and Y are $NR_{21}$; and wherein $R_{0-2}$ and $R_{21}$ are independently selected from the group consisting of, substituted or unsubstituted, aryl, heteroaryl, heterocyclyl, diarylamine, diheteroarylamine, dialkylamine, heteroarylalkylamine, arylalkylamine, H, F, cycloalkyl, halocycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, and trialkylsilylalkynyl; or wherein $R_{0-2}$ and $R_{21}$ alone or in combination, form art of a (hetero)aliphatic or (hetero)aromatic rings system.

5. An organic semiconductive material, wherein the organic semiconductive material comprises at least one organic matrix compound and a dopant, wherein the dopant is a heterocyclic compound, or a dimer, oligomer, polymer, dispiro compound, or polycycle thereof; having a structure according to the following formula:

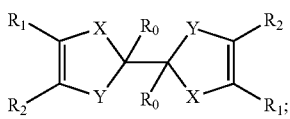

wherein X and Y are $NR_{21}$; and wherein $R_{0-2}$ and $R_{21}$ are independently selected from the group consisting of, substituted or unsubstituted, aryl, heteroaryl, heterocyclyl, diarylamine, diheteroarylamine, dialkylamine, heteroarylalkylamine, arylalkylamine, H, F, cycloalkyl, halocycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, and trialkylsilylalkynyl; or wherein $R_{0-2}$ and $R_{21}$ alone or in combination, form part of a (hetero)aliphatic or (hetero)aromatic ring system.

6. The organic semiconductive material according to claim 5, wherein the molar doping ratio of dopant to matrix molecule or the doping ratio of dopant to monomeric units of a polymeric matrix molecule is between 1:1 and 1:100,000.

7. An electronic or optoelectronic component, wherein the electronic or optoelectronic component comprises an electronically functionally active area, wherein the electronically active area comprises at least one heterocyclic compound, or a dimer, oligomer, polymer, dispiro compound, or polycycle thereof, having a structure according to the following formula:

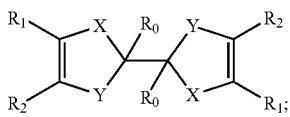

wherein X and Y are $NR_{21}$; and wherein $R_{0-2}$ and $R_{21}$ are independently selected from the group consisting of, substituted or unsubstituted, aryl, heteroaryl, heterocyclyl, diarylamine, diheteroarylamine, dialkylamine, heteroarylalkylamine, arylalkylamine, H, F, cycloalkyl, halocycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, and trialkylsilylalkynyl; or wherein $R_{0-2}$ and $R_{21}$ alone or combination, form part of a (hetero)aliphatic or (hetero)aromatic ring system.

8. The electronic or optoelectronic component according to claim 7, wherein the electronically active area comprises an organic semiconductive matrix material which is doped with at least one dopant to modify the electronic properties of the semiconductive matrix material, wherein the dopant comprises the at least one heterocyclic compound, or the dimer, oligomer, polymer, dispiro compound, or polycycle thereof.

9. The electronic or optoelectronic component according to claim 7, wherein the electronic or optoelectronic component is an organic light-emitting diode, a photovoltaic cell, an organic solar cell, an organic diode, an organic field effect transistor, or a photoinitiated and magnetic memory.

10. The electronic or optoelectronic component according to claim 4, wherein the heterocyclic compound is present as cation.

11. The organic semiconductive material according to claim 5, wherein the dopant is present as cation.

12. The electronic or optoelectronic component according to claim 7, wherein the at least one heterocyclic compound, or the dimer, oligomer, polymer, dispiro compound, or polycycle thereof is present as cation.

13. The heterocyclic compound, or a dimer, oligomer, polymer, dispiro compound, or polycycle thereof according to claim 1, wherein $R_{0-2}$ and $R_{21}$, alone or in combination, form part of a (hetero)aliphatic or (hetero)aromatic ring system.

* * * * *